United States Patent [19]

Rosenthal

[11] Patent Number: 4,863,722

[45] Date of Patent: Sep. 5, 1989

[54] DENTIFRICE COMPOSITIONS

[75] Inventor: Murray W. Rosenthal, Middlesex County, N.J.

[73] Assignee: Jeffrey Martin, Inc., Union, N.J.

[21] Appl. No.: 7,511

[22] Filed: Jan. 28, 1987

[51] Int. Cl.$^4$ .......................... A61K 7/16; A61K 7/18
[52] U.S. Cl. ........................................ 424/49; 424/52
[58] Field of Search ................................... 424/49, 52

[56] References Cited

U.S. PATENT DOCUMENTS

| | | | |
|---|---|---|---|
| 3,450,813 | 6/1969 | Muhler | 424/49 |
| 3,541,017 | 11/1970 | Muhler | 424/49 |
| 3,647,381 | 3/1972 | Retter | 424/49 |
| 3,892,843 | 7/1975 | Muhler et al. | 424/52 |
| 3,904,747 | 9/1975 | Cordon et al. | 424/49 |
| 3,954,961 | 5/1976 | Colodney et al. | 424/49 |
| 3,957,968 | 5/1976 | Cordon | 424/49 |
| 4,075,316 | 2/1978 | Cordon | 424/49 |
| 4,170,634 | 10/1979 | Cordon et al. | 424/49 |
| 4,187,288 | 2/1980 | Cordon et al. | 424/49 |
| 4,418,053 | 11/1983 | Muhler | 424/52 |

*Primary Examiner*—Shep K. Rose
*Attorney, Agent, or Firm*—Polster, Polster and Lucchesi

[57] ABSTRACT

An improved dentifrice contains, by weight, from about 0.02% to about 0.08% zirconium silicate of a mean particle size of 0.60 to 0.75 microns, no more than 25% of the particles being smaller than 0.4 microns nor more than 25%, larger than 1.0 micron, and at least 22% of synthetic, amorphous, precipitated hydrated silica, of at least 99% pure silicon dioxide on a dry basis, the mean particle size of which is in the range of 6-12 microns. The dentifrice may contain an alkaline zinc citrate.

5 Claims, No Drawings

DENTIFRICE COMPOSITIONS

BACKGROUND OF THE INVENTION

The process of cleaning human dentition with a toothbrush and dentifrice is an important function for both physiological and cosmetic purposes. Human teeth are exposed to a constant flow of saliva and rapidly accumulate a strongly-adherent proteinaceous salivary pellicle which is then colonized by oral bacterial to give rise to dental plaque. Both pellicle and plaque can be stained by a large number of intrinsic and extrinsic materials in the mouth, and if not removed regularly by the mechanical action of toothbrush and dentifrice, can become stained and unsightly. Of equal or greater importance, the presence of plaque on human teeth can lead to serious dental diseases. Some types of plaque contain bacteria which are acid-producing from the degradation of orally ingested carbohydrate foods, and the acid thus produced, along with virulent bacterial cells, can penetrate tooth structure and cause dental decay (caries). Other types of plaque contain bacteria which secrete enzymes that can attack the connective tissues of the human gingiva with the sequelae of tissue inflammation, bleeding, separation of the gingival tissue from the necks of teeth, the development of gingivitis and periodontal disease and in time, the restoration of supporting bony structure followed by the loss of teeth.

Brushing the teeth with a toothbrush alone does not keep the teeth free of stain. Similarly, the use of a dentifrice which lacks adequate abrasive action can result in inadequate cleaning with the subsequent development of cosmetically unacceptable stains.

It has been widely accepted that dentifrices should contain one or more abrasive agents to assist in the cleaning of the dentition. The question of a proper balance of dentifrice abrasivity and safety for human teeth, to avoid excessive wear and erosion of tooth structure, is a subject which has received continuing attention by dental authorities. Based on a comparison of products being tested against a standard, a reading of 250 or less by the Radioactive Dentin Abrasion (RDA) procedure is considered an acceptable level of abrasivity for a dentifrice. The procedure relies on an in vitro technique for irradiating human dentin and then measuring the amount of irradiated dentin removed from the teeth by a dentifrice when brushed on prepared human dentin specimens under standardized and reproducible brushing conditions.

It has been believed heretofore that the cleansing power of a dentifrice is directly proportional to its abrasive level, and that the best-cleaning dentifrices are also the most abrasive products. However, it has been discovered that this parallel relationship is not wholly accurate and it is an objective of this invention to demonstrate that exceptionally powerful cleaning systems can be prepared which have fully acceptable levels of abrasivity as measured by the RDA procedure.

The abrasive characteristics of dentifrice abrasive agents are related to the chemical nature of agents used, their particle size, their hardness and the shape of individual particles.

SUMMARY OF THE INVENTION

In accordance with this invention, generally stated, a superior cleansing oral composition in the form of a dentifrice gel or paste is provided, comprising:

(a) From about 0.02% to about 0.08% of a zirconium silicate of a mean particle size of 0.60–0.75 microns in which no more than 25% of the particles are smaller than 0.4 microns and no more than 25% of the particles are larger than 1.0 micron (b) At least 22%, and preferably from 22% to 50%, of synthetic, amorphous, precipitated hydrated silica, of at least 99% pure silicon dioxide (dry basis) content in which the mean particle size is in the range of 6–12 microns.

(c) The balance of the dentifrice gel or paste consisting of other ingredients commonly used in typical dentifrice compositions which may include but are not limited to water, humectants, flavors, sweeteners, foaming agents, colors, opacifiers, gums, thickeners and one or more pharmacologically active ingredients selected from the classes of water soluble fluorides, plaque and calculus inhibitors, antimicrobial compounds, deodorant ingredients, and non-steroidal anti-inflammatory drugs.

All percentages given are percentages by weight of the fully compounded dentifrice gel or paste.

DESCRIPTION OF THE PREFERRED EMBODIMENTS

It is the purpose of this invention to provide novel dentifrice compositions intended for application to the oral dentition with a toothbrush, which compositions possess superior cleansing properties against stains on teeth, more particularly those arising from tobacco tars, coffee, tea and other stains of extrinsic origin. Such compositions are also highly effective in the cleaning and removal of deposits which arise from biological activity within the oral cavity, such as are associated with the production and deposition of dental pellicle, dental plaque and dental calculus.

A particular feature of the invention is to employ within specified levels, combinations of a fine particle, synthetic, precipitated, hydrated silica and a zirconium silicate of controlled particle size. Such mixtures may also be employed with a complex zinc salt chemically identified as an alkali metal zinc citrate or with other pharmacologically active agents. Although each of these materials has been described in previous patents as a dentifrice ingredient, it was entirely unexpected that their use together, within the concentrations and particle sizes herein specified, would produce cleaning efficiency at heretofore unknown levels of efficacy.

U.S. Pat. Nos. 3,257,282, 3,330,732, 3,450,813 and 3,541,017 have described the incorporation of zirconium silicate in compositions for cleaning both natural and artificial teeth. However, the particle size of the zirconium silicate characterized in those patents may range as high as 75 microns and the concentration prescribed for use in compositions for cleaning natural or artificial teeth is described as being at least 0.5% of the total cleaning composition. U.S. Pat. No. 3,450,813, for example, suggests that zirconium silicate of the form there described enhances the dental cleaning and polishing capabilities of agents such as (certain calcium and sodium compounds and resins, or talc) but recommends the use of more than 1.6% of zirconium silicate in the dentifrice, "with the best results being obtained where the overall compositions comprise in excess of about 10% and preferably at least about 20% zirconium silicate."

It has been discovered, however, that if zirconium silicate of an extremely fine, but controlled, particle-size, is employed in suitable compositions, concentrations as low as 0.02%, and preferably, in the range of 0.02%–0.08% of the dentifrice composition are extremely effective as dentifrice cleaning adjuvants when used with a suitable silica abrasive agent and other dentifrice components.

The specific mean particle size of such zirconium silicate should range from 0.60 to 0.75 microns, and more specifically, no more than 25% of the particles should be smaller than 0.4 microns and no more than 25% of the particles should be larger than 1.0 micron. As a consequence of the low and controlled particle-size, dentifrices made with 0.02%–0.08% of this specific type of zirconium silicate have exceptional cleansing effectiveness and only moderate abrasivity. Dentifrices made with zirconium silicate of a mean particle size significantly larger than that described in the present invention have abrasivity characteristics which may cause excessive wear on the human dentition, while dentifrices made with zirconium silicate of a mean article size significantly smaller than that described herein are devoid of the outstanding cleaning effectiveness exhibited by compositions of this invention.

It also has been discovered that the utilization of 0.02%–0.08% zirconium silicate of an average particle size of 0.60 to 0.75 microns in dentifrice compositions wherein the bulk of the dentifrice abrasive system is a mixture of synthetic, amorphous precipitated hydrated silicas, in a concentration of from 22% to 50%, does not significantly impair the transparency of the dentifrice if it should be desired to formulate a transparent or translucent gel-type product. Typical characteristics of the zirconium silicate of the current invention include:

| ZIRCONIUM SILICATE SPECIFICATION | |
| --- | --- |
| Density gm/cc | 4.60 |
| Dielectric Constant | 12.7 |
| Hardness, MOHS | 7.5 |
| Melting Point | 1538°–1677° C. |
| Molecular Weight | 183.1 |
| Reflectance, IR | 60–75% |
| Reflectance UV | 80–85% |
| Refractive Index | 2.00 |
| Particle Size | |
| Smaller than 0.4 microns | No more than 25% |
| Larger than 1.0 micron | No more than 25% |
| Within 0.4–1.0 microns | At least 50% |

With specific regard to the fine-particle size synthetic, precipitated hydrated silicas proposed in this invention, it is important to incorporate at least 22% of such 22% material in dentifrice compositions, in the preferred range of to 50%, in combination with the type of zirconium silicate previously described, in order to achieve the exceptional cleansing effectiveness of the claimed invention. U.S. Pat. No. 3,538,230 describes oral compositions which contain synthetic, amorphous, precipitated hydrated silicas similar to those utilized in the dentifrice of this invention, but the preferred range of such material is described as 8% to 20%, and there is no mention of the use of zirconium silicate in combination with the synthetic precipitated silica.

For the purposes of this invention, the silicas employed are characterized as those produced in a liquid phase process and are described in the Cosmetic, Toiletry and Fragrance Association cosmetic ingredient dictionary as "hydrated silicas." They are prepared by reacting sodium silicate with sulfuric acid to produce silicon dioxide of an amorphous physical structure.

Typical characteristics of the silicas employed in this invention include:

| HYDRATED SILICA SPECIFICATIONS | |
| --- | --- |
| Total Volatiles | 33.0–37.0% |
| pH (5% in water) | 8.0–9.5 |
| Wet Screen Test | |
| Thru 325 Mesh | 99.5% min. |
| Heavy Metals | 50 ppm. max. |
| Particle Size | 6–12 microns |
| Silicon Dioxide Content (dry basis) | 99.0% min. |

Hydrated silicas of the type described herein are available commercially from the W. R. Grace & Company Davison Chemical Division and the J. M. Huber Company. A particularly valuable property of the hydrated silicas when used in viscous, semi-solid dentifrice compositions is that they have refractive indices of such magnitude that it is possible to compound them with a suitable liquid vehicle which has a refractive index value similar to that of the hydrated silica, to achieve transparent or translucent gel-type dentifrice. Such transparent or translucent products can be readily converted into opaque dentifrice pastes by the addition of titanium dioxide, zinc oxide, magnesium oxide or other water-insoluble, opacifying agents.

Another component which can be incorporated into the preferred cleansing dentifrices, if desired, is the complex molecule, alkali metal zinc citrate, the preparation, utilization and chemical properties of which have been described in U.S. Pat. No. 4,325,939.

In the preferred embodiment of this invention, the highest cleaning dentifrices utilize those components specifically claimed in this invention: the zirconium silicate of fine but controlled particle size, and the hydrated silica at a minimum level of 22%, each with specified chemical and physical characteristics as specified herein.

It is desirable, but not critical, to employ in the preferred embodiment of this invention, a water-soluble fluoride for the purpose of inhibiting dental caries. It is also desirable, but not critical, to employ in the preferred embodiment of this invention, the alkali metal salt of a zinc citrate complex, e.g. sodium zinc citrate or potassium zinc citrate, for its effects in suppressing oral malodor by the interaction and precipitation of volatile sulfur compounds (VSC's) by zinc ions, and its effects in inhibiting the deposition of dental calculus by preventing the crystallization of the hydroxyapatite of calcium phosphate.

In order to achieve cosmetically elegant dentifrice gels and pastes, it is advisable to incorporate into finished compositions, other agents customarily used for semi-solid dentifrice paste and gel products. Therefore, deionized or distilled water is incorporated at a level of 0–50%, and humectants such as glycerin, sorbitol, mannitol, polyethylene glycols and the like are incorporated at levels of 10–60%. Other soluble and insoluble ingredients may include a suitable foaming agent, such as sodium lauryl sulfate, sodium lauroyl sarcosinate or nonionic surfactants, a thickener such as one of the water-soluble synthetic cellulose derivatives, sodium alginate, carageenan, xanthan gum, carbomer 940, the copolymer of polyvinylpyrrolidone-maleic anhydride, or the like. Typical flavors such as peppermint, spearmint, cinnamaldehyde, wintergreen and the like, sweeteners such as saccharin, aspartame, cyclamates, and approved dyes may also be utilized in the current invention. Other ingredients which may be used for oral therapy needs include pyrophosphates to inhibit dental calculus formation, non-steroidal anti-inflammatory drugs, water-soluble copper salts as odor suppressants, urea or other alkalinizing agents to inhibit microbial acid production, sanguinaria or zinc salts as plaque suppressants and antibacterial agents including antibiotics, quaternary ammonium compounds (used with a nonionic foaming agent) and various phenolic compounds.

Typical compositions made in accordance with the teachings of this invention are offered below:

EXAMPLE I

EXAMPLE I

| Translucent Dentifrice Gel | |
|---|---|
| Hydrated Silica | 30.00% |
| Zirconium Silicate | 0.04% |
| Water | 16.71% |
| Sorbitol 70% | 40.00% |
| Glycerin | 10.00% |
| Sodium Lauryl Sulfate | 1.00% |
| Flavor | 1.00% |
| Carageenan | 1.00% |
| Saccharin | 0.25% |
| | 100.00% |

EXAMPLE II

EXAMPLE II

| Translucent Dentifrice Gel | |
|---|---|
| Water | 8.12% |
| Sodium Zinc Citrate | 1.00% |
| Glycerin | 10.00% |
| Sorbitol 70% | 45.00% |
| Xanthan Gum | 0.75% |
| Sodium Fluoride | 0.22% |
| Sodium Saccharin | 0.25% |
| Hydrated Silica | 25.00% |
| Air-Borne Silica | 7.00% |
| Sodium Lauroyl Sarcosinate | 1.00% |
| Flavor | 1.10% |
| Dye Solution | 0.50% |
| Zirconium Silicate | 0.06% |

EXAMPLE III

| Opaque Toothpaste | |
|---|---|
| Zirconium Silicate | 0.05% |
| Hydrated Silica | 30.00% |
| Glycerin | 15.00% |
| Sorbitol 70% | 25.00% |
| Hydroxyethylcellulose | 1.00% |
| Zinc Chloride | 0.50% |
| Citric Acid | 2.00% |
| Hexylresorcinol | 0.05% |
| Sodium Monofluorophosphate | 0.76% |
| Pluronic F68 | 1.50% |
| Flavor | 1.00% |
| Titanium Dioxide | 0.50% |
| Sodium Saccharin | 0.30% |
| Water | 22.34% |

Example I is a dentifrice gel with superior cleaning properties against dental stains. Example II represents a dentifrice gel with high cleaning which also contains sodium fluoride as a caries-inhibitory agent and sodium zinc citrate as an odor neutralizer. Example III is a toothpaste which contains zinc chloride as an inhibitor of dental plaque and calculus, hexyl resorcinol as an antibacterial agent and titanium dioxide as an opacifying agent.

Dentifrices of this invention have been evaluated for their cleaning performance against stained pellicle in accordance with the method described by Stookey, Burkhard and Schemehorn (J. Dent. Res. 61:1236–1239, Nov., 1982). In this procedure, bovine permanent incisors are cut to obtain labial enamel specimens approximately 10 mm$^2$. The specimens are mounted in autopolymerizing methacrylate resins so that enamel is exposed. After cleaning and polishing, the enamel surfaces are etched with 1% hydrochloric acid, neutralized with sodium carbonate and re-etched with 1% phytic acid and rinsed. Specimens are then alternately and repeatedly immersed at 37° C. in a staining bath followed by air-drying. The staining solution contains instant coffee, instant tea, ferric chloride and gastric mucin dissolved in a trypticase soy broth inoculated with a Sarcinia Lutea turtox culture. After a substantial level of brown stain develops on test specimens, the now-pigmented specimens are dried and then mounted in a mechanical cross-brushing machine with a slurry of 25 g of test dentifrice and 40 ml of water, and brushed for 800 reciprocating double strokes. A slurry of a standard lot of calcium pyrophosphate serves as a standard against which all test dentifrices are compared. The efficiency of cleaning is determined by comparing stain levels before and after brushing, as follows:

$$\frac{\text{Mean Decrement for Test Material}}{\text{Mean Decrement for Reference Standard}} \times 100 =$$

Cleaning Ratio

Good correlation has been demonstrated between results obtained by this method and in vivo clinical cleaning efficiency. When this method was used to compare the cleaning results of a large number of dentifrices with different abrasive systems, it was found that dentifrices prepared in accordance with the teachings of this invention produced the most effective levels of cleaning, as demonstrated in Table I.

TABLE I
CLEANING EFFICIENCY OF DENTIFRICES PREPARED WITH DIFFERENT ABRASIVE SYSTEMS AGAINST STAINED PELLICLE

| DENTIFRICE AND ABRASIVE SYSTEM | CLEANING EFFICIENCY |
|---|---|
| Zirconium Silicate - Hydrated Silica Dentifrice (1) | 165, 163, 160* |
| Calcium Pyrophosphate Dentifrice (2) | 141 |
| Hydrated Silica - Tetrasodium Pyrophosphate Dentifrice (2) | 122 |
| Hydrated Silica Dentifrice (2) | 115 |
| Dicalcium Phosphate Anhydrous-Dicalcium Phosphate Dihydrate Dentifrice (2) | 115 |
| Reference Standard (3) | 100 |
| Dicalcium Phosphate Dihydrate - Calcium Carbonate Dentifrice (2) | 82 |
| Dicalcium Phosphate Dihydrate Dentifrice (2) | 74 |
| Aluminum Hydroxide, Dicalcium Phosphate Dihydrate Dentifrice (2) | 62 |

*Results of separate evaluations
(1) Dentifrices prepared with abrasive systems in accordance with this invention
(2) Leading commercial dentifrice
(3) Calcium pyrophosphate slurry Cleaning studies have also been done by an in vitro evaluation method in which tobacco tar stain serves as the pigmented substrate. The method of preparing stained bovine enamel with cigarette tar is similar to that described above, except that an alcoholic extract of cigarette tobacco is used instead of coffee and tea, and human saliva serves as the protein source rather than gastric mucin and bacteriological nutrient media. The method, which will be published, has been described as producing a typical tobacco tar stain which is very heavy and tenacious.

Dentifrices prepared in according with the teachings of this invention have been compared to a number of commercial dentifrice abrasive systems and have been found to exhibit superior cleaning as indicated in Table II.

TABLE II

CLEANING EFFICIENCY OF DENTIFRICES PREPARED WITH DIFFERENT ABRASIVE SYSTEMS AGAINST TOBACCO TAR-SALIVARY PROTEIN STAIN

| DENTIFRICE AND ABRASIVE SYSTEM | CLEANING EFFICIENCY |
| --- | --- |
| Zirconium Silicate-Hydrated Silica Dentifrice (1) | 212, 213, 204* |
| Hydrated Silica-Sodium Pyrophosphate Dentifrice (2) | 159, 155* |
| Hydrated Silica Dentifrice (2) | 103, 117, 105* |
| Zirconium Oxide-Hydrated Silica Dentifrice (2) | 116 |
| Reference Standard (3) | 100 |
| Dicalcium Phosphate Anydrous-Dicalcium Phosphate Dihydrate Dentifrice (2) | 98 |
| Aluminum Hydroxide, Dicalcium Phosphate Dihydrate Dentifrice (2) | 49 |
| Dicalcium Phosphate Dihydrate Dentifrice (2) | 40 |
| Hydrated Silica, Calcium Carbonate Dentifrice (2) | 45 |

*Results of separate evaluations
(1) Dentifrices prepared with abrasive systems in accordance with this invention
(2) Leading commercial dentifrice
(3) Calcium pyrophosphate slurry It will be observed that the abrasive systems of this invention have levels of cleaning efficiency against in vitro coffee-tea-protein stained pellicle and in vitro protein-tobacco tar stains which are significantly better than abrasive systems currently used in existing commercial dentifrices. However, despite this superior performance, the levels of radioactive dentin abrasion of the dentifrices of this invention are in the range of 160–180, considerably lower than the level of 250 believed to be safe for use on human teeth.

Numerous variations in the composition of the dentifrice of this invention, within the scope of the appended claims, will occur to those skilled in the art in the light of the foregoing disclosure. The term "semi-solid" is used herein to embrace transparent, translucent and opaque gels and pastes. As has been suggested, in compounding suitable semi-solid dentifrice of this invention, innumerable combinations of foaming agents, humectants, thickeners, flavoring agents, dyes, therapeutic agents, odor suppressants, disinfectants, plaque suppressants, opacifiers and the like can be employed. Those set out specifically are merely illustrative.

Having thus described the invention what is claimed and desired to be secured by Letters Patent is:

1. A semi-solid dentifrice having an abrasive component consisting essentially of, by weight of the fully compounded dentifrice, about 0.02% to about 0.08% zirconium silicate of a mean particle size of about 0.60 to 0.75 microns, no more than about 25% of the particles being smaller than 0.04 microns and no more than about 25% being larger than 1.0 micron, and at least 22% synthetic, amorphous, precipitated hydrated silica, of at least 99% pure silicon dioxide on a dry basis, the mean particle size of which is in a range of about 6 to 12 microns, said dentifrice having a radioactive dentin abrasion on the order of 160–180.

2. The dentifrice of claim 1 including an alkali metal zinc citrate.

3. The dentifrice of claim 1 wherein the balance of the constituents comprises at least one humectant, thickener, flavoring agent and foaming agent.

4. The dentifrice of claim 1 which is a translucent gel.

5. The dentifrice of claim 1 including an opacifying agent.

* * * * *

UNITED STATES PATENT AND TRADEMARK OFFICE
CERTIFICATE OF CORRECTION

PATENT NO. : 4,863,722
DATED : September 5, 1989
INVENTOR(S) : Murray W. Rosenthal It is certified that error appears in the above-identified patent and that said Letters Patent is hereby corrected as shown below:

Column 1, line 28, "restoration" should be --resorption--.

Column 1, line 45, "in vitro" should be --*in vitro*--.

Column 3, line 51, "of such 22% material" should be --of such material--.

Column 3, line 52, "to 50%" should be --22% to 50%--.

Column 6, line 36, "in vivo" should be --*in vivo*--.

Column 6, line 65, "in vitro" should be --*in vitro*--.

Column 7, lines 36-37, "in vitro" should be --*in vitro*--.

Column 7, line 37, "in vitro" should be --*in vitro*--.

Signed and Sealed this

Fourth Day of September, 1990

Attest:

HARRY F. MANBECK, JR.

Attesting Officer     Commissioner of Patents and Trademarks